United States Patent [19]
Mitchell

[11] Patent Number: 6,030,366
[45] Date of Patent: Feb. 29, 2000

[54] SYRINGE GUARD SYSTEM FOR A UNIT DOSE SYRINGE

[75] Inventor: David W. Mitchell, Orange, Calif.

[73] Assignee: Safety Syringes, Inc., Oceanside, Calif.

[21] Appl. No.: 09/188,830

[22] Filed: Nov. 9, 1998

[51] Int. Cl.[7] .................................................. A61M 5/00
[52] U.S. Cl. ............................................ 604/192; 604/232
[58] Field of Search ..................................... 604/192, 198, 604/263, 110, 232, 218, 207, 187

[56] References Cited

U.S. PATENT DOCUMENTS

| | | |
|---|---|---|
| 2,571,653 | 2/1951 | Bastien . |
| 3,885,562 | 5/1975 | Lampkin . |
| 4,048,997 | 9/1977 | Raghavachari et al. . |
| 4,631,057 | 12/1986 | Mitchell . |
| 4,681,567 | 7/1987 | Masters et al. . |
| 4,702,738 | 10/1987 | Spencer . |
| 4,874,384 | 10/1989 | Nunez . |
| 4,923,445 | 5/1990 | Ryan . |
| 4,969,877 | 11/1990 | Kornberg . |
| 5,000,744 | 3/1991 | Hoffman et al. . |
| 5,002,537 | 3/1991 | Hoffman et al. . |
| 5,013,301 | 5/1991 | Marotta, Jr. et al. . |
| 5,098,382 | 3/1992 | Haber et al. . |
| 5,201,720 | 4/1993 | Borgia et al. . |
| 5,215,535 | 6/1993 | Gettig et al. . |
| 5,269,766 | 12/1993 | Haber et al. . |
| 5,344,407 | 9/1994 | Ryan . |
| 5,385,557 | 1/1995 | Thompson . |
| 5,417,660 | 5/1995 | Martin . |
| 5,433,712 | 7/1995 | Stiles et al. . |
| 5,437,647 | 8/1995 | Firth et al. . |
| 5,445,620 | 8/1995 | Haber et al. . |
| 5,496,286 | 3/1996 | Stiehl et al. . |
| 5,498,244 | 3/1996 | Eck . |
| 5,514,107 | 5/1996 | Haber et al. . |
| 5,552,812 | 9/1996 | Tolonn et al. . |
| 5,569,211 | 10/1996 | Lekhgolts et al. . |
| 5,624,400 | 4/1997 | Firth et al. . |
| 5,855,839 | 1/1999 | Brunel . |

FOREIGN PATENT DOCUMENTS

| | | |
|---|---|---|
| 0 740 942 A1 | 11/1996 | European Pat. Off. . |
| 2 283 425 | 10/1995 | United Kingdom . |
| WO 95/04565 | 2/1995 | WIPO . |

*Primary Examiner*—John D. Yasko
*Attorney, Agent, or Firm*—Lyon & Lyon LLP

[57] ABSTRACT

A guard for a medical cartridge, such as a pre-filled syringe, includes a body having an open proximal end communicating with a cavity for receiving the cartridge, and a shield slidably attached to the body. The body has a semi-rigid cantilever member on its distal end from which a stop tab, having a sloped distal edge and a blunt proximal edge, extends. The shield includes an elongate opening for receiving the stop tab, thereby allowing the shield to slide between unguarded and guarded positions for exposing and covering a needle, respectively. During assembly of the shield and body, the stop tab slidably engages an assembly tab on the shield, deflecting the cantilever member inward while the stop tab passes under the shield, the sloped distal edge of the stop tab minimizing damage to the stop tab or shield. In the guarded position, the blunt proximal edge of the stop tab engages a proximal wall of the elongate opening to prevent further distal movement beyond the guarded position. The body and shield include cooperating detents and distal detent pockets having oblique proximal corners that mutually engage to prevent proximal movement from the guarded position. Proximal detent pockets are also provided that include sloped distal edges terminating in blunt distal corners. The detents include sloped distal edges terminating in blunt distal corners that engage the distal corners of the proximal detent pockets to create an initial resistance to distal movement from the unguarded position.

40 Claims, 10 Drawing Sheets

SYRINGE GUARD SYSTEM FOR A UNIT DOSE SYRINGE

FIELD OF THE INVENTION

The present invention relates generally to syringes, and more particularly to an improved syringe guard for a medical cartridge, such as a un t dose pre-filled syringe, including a shield for covering the needle thereof after medication is dispensed from the syringe.

BACKGROUND

Medication is often dispensed using a unit dose medical cartridge, such as an ampule, vial or syringe, and a syringe holder, injector or adapter. The cartridge typically has a barrel with a needle at one end and a plunger at the other end. Such cartridges are often referred to as "pre-filled syringes" because they contain a specific dosage or volume of medication when they are initially provided, as compared to conventional syringes which are furnished empty and filled by the user prior to use. Alternatively, the medical cartridge may include a rubber stopper instead of a needle and/or may include a piston rather than a plunger on the other end. The syringe adapter is typically a hollow body adapted to hold the cartridge, including a plunger to engage and move the piston in the cartridge.

Because of the threat of communicable diseases, a number of syringes and adapters have been developed to prevent accidental needle sticks or inadvertent reuse of needle devices. Many of these devices, however, are not easy to use or are complicated to manufacture. For example, U.S. Pat. No. 5,569,211 discloses a syringe that allows the needle of the syringe to be withdrawn into the barrel of the syringe after medication is dispensed from it. This device, however, is a specially designed substitute for a conventional syringe, and cannot be used to hold commercially available pre-filled syringes or ampules.

U.S. Pat. No. 5,522,812 discloses a complicated syringe shield device for holding a conventional cartridge not having its own needle. The device has a number of complicated parts, including a cylindrical body, a double needle assembly, a cylindrical shield, a special collar piece allowing the shield to be drawn over the needle and locked, and a plunger assembly, resulting in a device that is potentially difficult and expensive to manufacture. The device also requires two hands to operate, one to hold the body, and one to rotate the shield into the locked position, which may be inconvenient to the medical professional using the device.

Another consideration with unit dose cartridges and pre-filled syringes is that they are often made from glass, particularly for holding certain vaccines or biotech drugs where concern about micro-organisms or other contaminants is most critical. Glass pre-filled syringes may be particularly fragile and often may break during transportation or use. Some existing adapters may not adequately protect the syringe contained therein from such risks. Others, provide greater protection for the cartridge, but may obstruct the medical professional's view of the syringe when the device is being used, hampering monitoring of the medication being delivered.

Therefore, there is a need for an improved safety syringe which is inexpensive and simple to manufacture.

In addition, there is a need for a syringe guarding mechanism which provides improved protection for the cartridge or pre-filled syringe therein, but allows effective observation of the syringe and the medication being dispensed.

SUMMARY OF THE INVENTION

The present invention is directed to a guard or adapter for a medical cartridge, such as a unit dose pre-filled syringe, an ampule and the like, that may be used to inject medication or other drugs into a patient. Generally, the guard includes two parts, namely a housing or body for receiving and holding the cartridge, and a protective case or shield slidably attached to the body. The body, preferably an elongate rectangular member, has a cavity therein for receiving the cartridge, an open proximal end communicating with the cavity, and a distal end. Preferably, the distal end has an opening through which a needle on the cartridge may extend when the cartridge is received in the cavity, although alternatively the body may include a double ended needle for penetrating a rubber stopper on a cartridge without its own needle.

The shield, preferably a rectangular tubular member, is slidably attached to the body, and has open proximal and distal ends, the distal end having an opening through which the needle may extend when the shield is in an unguarded position. The shield is slidable with respect to the body between the unguarded position and a guarded position wherein the needle is covered by the shield.

A semi-rigid cantilever member may be provided on the distal end of the body, which preferably extends proximally from the distal end. The cantilever member has a stop tab extending substantially transversely therefrom, the stop tab preferably having a substantially ramped distal edge, preferably extending outward to a radiused outer edge, and a substantially blunt proximal edge. The shield includes an elongate opening for receiving the stop tab, the stop tab being slidable in the opening, thereby allowing the shield to slide between the unguarded and guarded positions.

In addition, cooperating detents and detent pockets may be formed in the body and shield for mutually engaging to hold the shield in the guarded position. Preferably, the detent pockets have substantially blunt proximal edges defining substantially blunt proximal corners, and the detents have substantially oblique proximal edges defining substantially acute proximal corners. When the shield is moved to the guarded position, the detents enter the detent pockets, and the proximal corners on the detents engage the proximal corners in the detent pockets to prevent substantial proximal movement of the shield from the guarded position.

In a preferred form, first and second sets of detent pockets are formed in the body, the second set, corresponding to the guarded position just described, being located distally from the first set. The first set of detent pockets have generally sloped distal edges that lead to substantially blunt recesses at the bottoms of the detent pockets, such that the distal edges terminate in substantially blunt distal corners. In addition, a plurality of detents are formed on the shield for engaging the detent pockets. The plurality of detents include generally sloped distal edges, the distal edges terminating in substantially blunt distal corners. Thus, when the shield is in the unguarded position, the detents enter the first set of detent pockets such that the distal corners of the detents substantially engage the distal corners of the detent pockets to create an initial resistance to movement of the shield from the unguarded position.

The shield is generally provided pre-assembled on the body, preferably by inserting the body into the shield until the stop tab enters the elongate window on the shield. During insertion, the ramped distal edge of the stop tab on the body slidably engages a tapered assembly tab on the shield, which deflects the cantilever member inward to facilitate the stop tab passing under the wall of the shield. The radiused outer edge of the stop tab minimizes damage, e.g., scuffing, to the stop tab and/or to the shield during insertion. When the stop tab enters the elongate window in the shield, the cantilever member resiliently returns to its original position, and the shield may then slide in relation to the body between the unguarded and guarded positions, limited by the stop tab engaging distal and proximal walls, respectively, of the elongate window.

The guard is generally provided with the shield in the unguarded position, preferably with the stop tab abutting the distal edge of the window and the detents engaging the first set of detent pockets. After the cartridge in the guard has been used to deliver its medication, the shield may be moved distally until it reaches the guarded position. In the guarded position, the stop tab on the body abuts the proximal edge of the elongate window, the substantially blunt proximal edge of the stop tab positively engaging the proximal wall of the elongate window, and thereby preventing further distal movement of the shield.

In the unguarded position, the distal corners of the detents engage the distal corners of the first set of detent pockets, creating an initial resistance to distal movement of the shield that may prevent unintentional activation of the shield. Once this initial resistance is overcome, the detents may easily leave the first set of detent pockets, the detents sliding up the sloping edges of the proximal detent pockets, and then sliding along the body until they enter the second set of detent pockets when the shield reaches the guarded position. The oblique proximal edges of the detents then substantially engage the blunt proximal edges of the second set of detent pockets, thereby preventing substantial proximal movement of the shield, i.e., back towards the unguarded position. Thus, the stop tab and the detents and detent pockets cooperate to substantially permanently lock the shield in the guarded position for disposal.

In a first preferred embodiment, the guard has only two parts, namely a body and a shield, which are pre-assembled in the unguarded position ready to receive a cartridge. The body includes a finger grip integrally molded to its proximal end, the finger grip preferably defining a "T" shape. A locking mechanism, such as integrally formed locking detents, are provided on the finger grip for substantially permanently engaging a flange on the cartridge. The cartridge is preferably a conventional unit dose pre-filled syringe, including its own needle and needle cover on its distal end, a flange on its proximal end, and its own plunger. The pre-filled syringe is inserted into the proximal end of the body until it is fully encapsulated within the cavity, and until the flange on the pre-filled syringe engages the locking detents on the finger grip, thereby substantially permanently locking the syringe into the guard. Once locked into the guard, the needle and needle cover of the pre-filled syringe extend at least partially through the distal openings in the body and shield. After medication is dispensed, the shield is slid into the guarded position, using one or two hands, preferably only requiring one hand, the pre-filled syringe and guard then being ready for disposal.

In a second preferred embodiment, the guard includes an attachable finger grip plug and a plunger, in addition to the body and shield. The cartridge is preferably a single dose ampule having its own needle and needle cover on its proximal end and a piston within its barrel. The finger grip plug and the proximal end of the body include cooperating members for locking the finger grip plug to the body and/or preventing the ampule within the body from moving substantially proximally.

The body and shield are generally provided pre-assembled in the unguarded position, as previously described, with the finger grip plug and plunger furnished separately. An ampule is inserted into the proximal end of the body until it is fully encapsulated within the cavity. The finger grip plug is attached to the body, substantially permanently enclosing the cavity and encapsulating the ampule therein, and the plunger is attached to the piston through the finger grip plug.

After medication is dispensed, the shield is slid into the guarded position, as with the first preferred embodiment, with one or two hands. The stop tab and/or cooperating detents and detent pockets operate, as described above, such that the shield may be substantially permanently locked in the guarded position to facilitate safe disposal of the ampule and guard.

Other objects and features of the present invention will become apparent from consideration of the following description taken in conjunction with the accompanying drawings.

BRIEF DESCRIPTION OF THE DRAWINGS

For a better understanding of the invention, and to show how it may be carried into effect, reference will be made, by way of example, to the accompanying drawings, in which.

DETAILED DESCRIPTION OF THE PREFERRED EMBODIMENTS

Turning to the drawings, FIGS. 1–6C show a preferred embodiment of a syringe guard 10 for holding a pre-filled unit dose syringe 90, in accordance with the present invention. Generally, the guard 10 includes two parts, namely a housing or body 20 for receiving and holding the pre-filled syringe 90, and a protective case or shield 60 slidably attached to the body 20. Both the body 20 and the shield 60 are generally molded from plastic, such as polypropylene, butadiene styrene or polycarbonate, and are preferably clear and substantially colorless to facilitate observation of the pre-filled syringe 90 received therein. Alternatively, they may be translucent or opaque, and may be colored, such as a latex color, or a flesh tone, such as off-white, brown, or black.

With particular reference to FIGS. 2A–2D, the body 20 is an elongate member, preferably having a substantially rectangular cross-section, including two side rails 28, an open proximal end 22, and an open distal end 24. The rectangular shape is preferred as it provides superior rigidity, protecting the pre-filled syringe 90 therein from lateral forces that might otherwise damage it, particularly if the pre-filled syringe 90 is made of glass. Alternatively, instead of the rectangular cross-section, the body 20 and shield 60 may have corresponding oval or round cross-sections (not shown) providing sufficient rigidity to protect the pre-filled syringe 90 received in the body 20.

In addition, the body 20 has a substantially rigid collar 32 on the distal end 24, and a finger grip 50 on the proximal end 22, both attached or preferably integrally molded to the body 20. Alternatively, instead of being formed from the side rails 28, the body 20 may be a substantially rectangular body having four side walls (not shown).

The two side rails 28 generally have a "C" shape and define a cavity 26 in the body 20, the cavity 26 extending axially from the proximal end 22 to the distal end 24 of the body 20. The inside surface 30 of the rails 28 is preferably concave, conforming substantially to the outer diameter of a standard unit dose pre-filled syringe. Alternatively, if the side rails 28 have a flat or "C" channel inside surface 30, guide rails (not shown) and the like may be provided on the inside surface 30 to facilitate insertion of the pre-filled syringe 90 into the cavity 26 and/or to support the pre-filled syringe 90 to prevent substantial lateral movement which may damage the pre-filled syringe 90.

The finger grip 50 generally includes a pair of wing-like members 52 integrally molded to the proximal end 22 of the body 20, thereby generally defining a "T" shape. Each wing-like member 52 includes a distal surface or finger ledge 54, and an outer gripping surface 56 extending proximally from the outer edge 54a of the finger ledge 54. The outer gripping surface 56 may include a lip, grooves or other irregularities (not shown) protruding from its proximal end or set in the surface 56, if desired to improve the hold on the finger grip 50. Lateral surfaces 55 extend proximally from the finger ledges 54 between the gripping surfaces 56E, thereby defining a recess or open proximal end 51 communicating with the cavity 26 in the body 20. The lateral surfaces 55 of the finger grip 50 include a plurality of locking detents 58 partially defining an aperture or slot 57 for holding the pre-filled syringe 90 inserted into the cavity 26, as described further below.

The collar 32 extending from the distal end 24 preferably has a substantially annular shape, including an opening 34 extending therethrough for allowing the needle 95 and needle cover (not shown) on the pre-filled syringe 90 in the cavity 26 to extend beyond the body 20. The opening 34 preferably has a diameter smaller than the cavity 26, such that the distal end 24 further retains the pre-filled syringe 90 inside the cavity 26, preventing distal movement. Alternatively, the distal end 24 may be tapered or otherwise partially obstructed to engage the distal end of the pre-filled syringe 90 and/or to prevent distal movement of the pre-filled syringe 90, without substantially interfering with the needle 95 and needle cover extending beyond the distal end 24.

In a further alternative, the distal end 24 may include an expandable "collet" (not shown) defined by a plurality of longitudinal slots extending proximally a short distance from the distal end 24. The collet may have a diameter smaller than that of the syringe barrel 92, hub 94 and/or needle cover as desired, thereby allowing the distal end 24 to be resiliently expanded to substantially engage the pre-filled syringe 90 received therein. In still another alternative, the opening 34 in the distal end 24 may have a sufficiently large diameter to freely allow the distal end of the pre-filled syringe 90 to extend therethrough, the pre-filled syringe 90 being locked substantially within the body 20 exclusively by a locking mechanism on the proximal end 22 or finger grip 50 of the body 20.

Figure 2A:
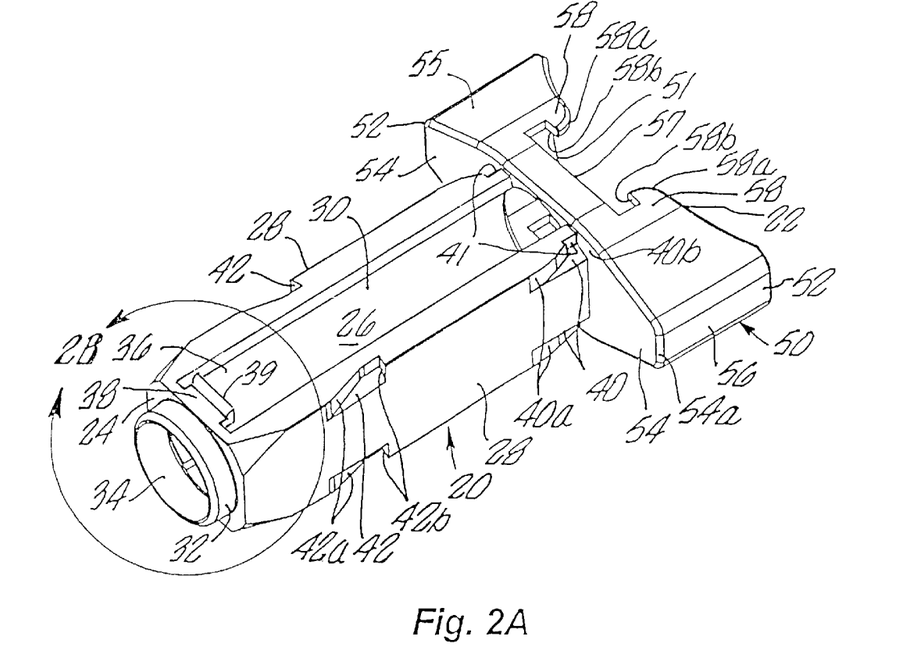
FIGS. 2A, 2B and 2C are perspective views of the body of the syringe guard of FIG. 1.
Figure 2B:
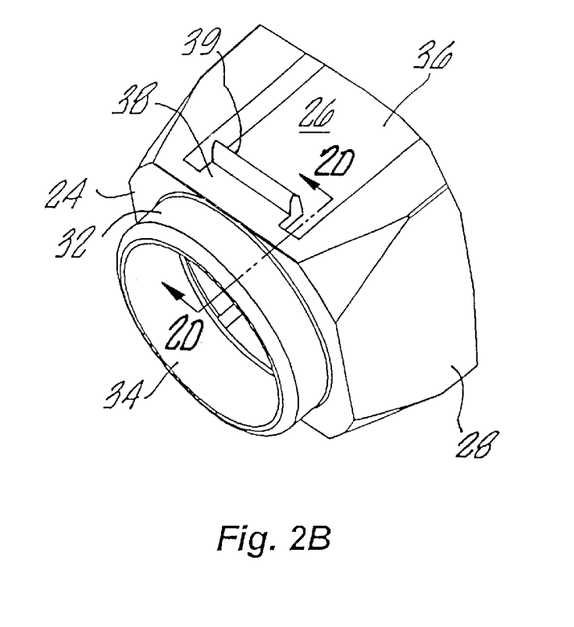
Figure 2C:
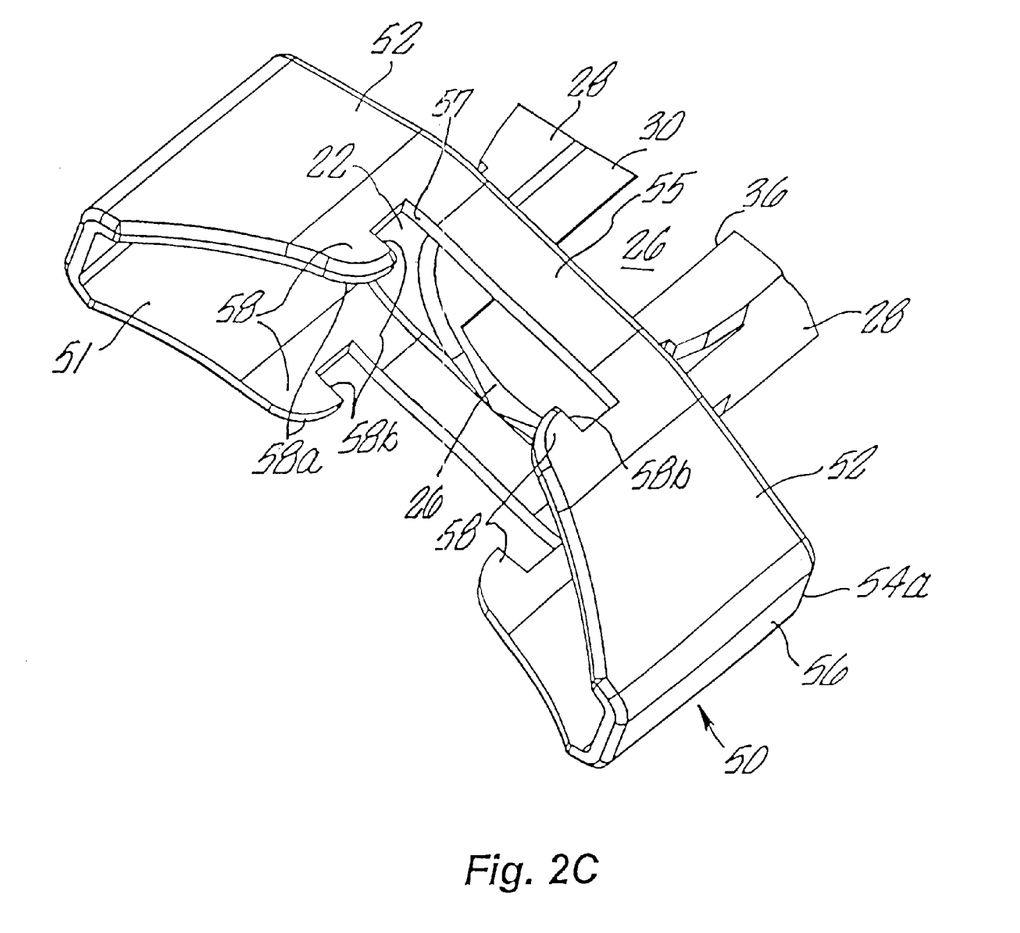

The side rails 28 define two elongate openings or windows 36 extending longitudinally between the finger grip 50 and the distal end 24, allowing observation of the pre-filled syringe 90 held in the body 20. Alternatively, if a four-walled body is provided (not shown), an elongate opening or window may be integrally formed in one or more of the side walls, preferably in two walls on opposite sides of the body.

The body 20 also includes one or more stop tabs 39 attached or integrally molded to the body 20. Preferably, a cantilever member 38 is integrally molded to the distal end 24 of the body 20 from which the stop tab 39 extends transversely outward. The cantilever member 38 extends proximally from the distal end 24, preferably within the window 36, and may have a tapered or substantially uniform width, for example, to the accommodate the shape of the distal end 24 of the body 20. The cantilever member 38 provides a semi-rigid support structure for the stop tab 39 that may be deflected inward, but resiliently returns to its original outward position.

Figure 2D:
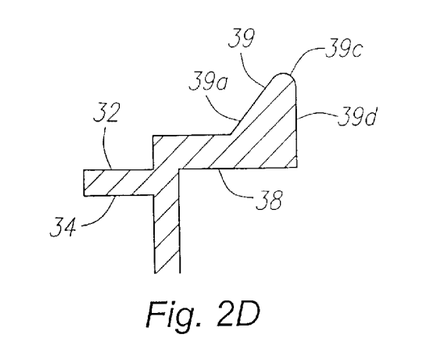
FIG. 2D is a cross-sectional view taken along line D—D of FIG. 2B, showing a cantilever member and stop tab on the body.

As best seen in FIG. 2D, the stop tab 39 has a sloped distal edge 39a and a generally blunt proximal edge 39b. More preferably, the distal edge 39a is substantially ramped and extends outward to a radiused outer edge 39c, and the proximal edge 39b is substantially blunt, i.e., extends substantially perpendicular to a longitudinal axis of the body. In an alternative form, shown in FIG. 2G, the distal edge 39a' may be generally convex in shape and/or the proximal edge 39b' may be generally concave, thereby defining a substantially acute outer corner 39c ' between the distal and proximal edges 39a', 39b' that extends in a generally proximal direction.

Figure 2E:
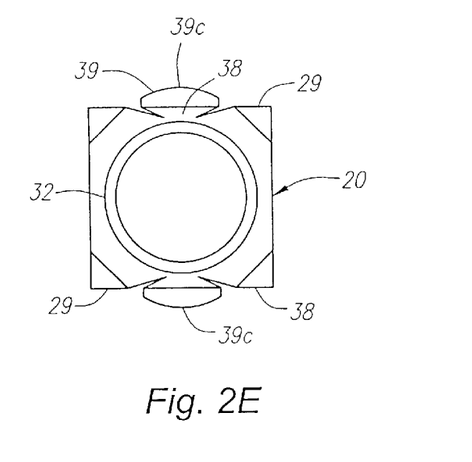
FIG. 2E is an end view of the body of the syringe guard of FIG. 2A.
Figure 2F:
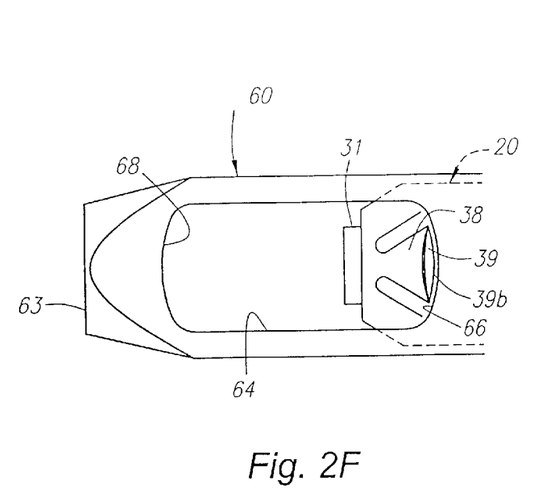
FIG. 2F is a side view of the body received in a slidable shield, showing a stop tab on the body abutting a proximal edge of an elongate window in the shield.
Figure 2G:
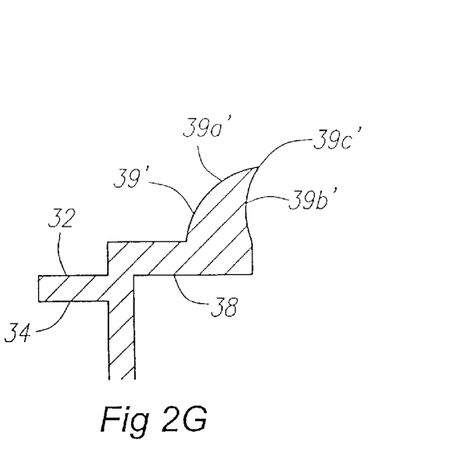
FIG. 2G is a cross-sectional view taken along line D—D of FIG. 2B, showing an alternative embodiment of a cantilever member and stop tab on the body.

In a preferred form, the outer edge 39c of the stop tab 39 is slightly convex to facilitate assembly, although alternatively, the outer edge 39c may also be substantially flat, i.e., extending substantially parallel to the upper surface 29 of the body 20. In addition, as shown in FIG. 2F, the proximal edge 39b of the stop tab 39 may have a slightly convex shape across the width of the cantilever member 38, corresponding substantially to the shape of a proximal wall 66 of an elongate window 64 in a shield 60, described further below. Alternatively, the proximal edge 39b may be substantially straight (not shown) and/or the distal edge 39a may be slightly convex corresponding substantially to a distal wall 68 of the elongate window 64. Preferably, as shown in FIG. 2E, a pair of cantilever members 38 and stop tabs 39 are molded onto the body 20 on two opposite sides of the distal end 24 of the body 20 within the windows 36.

Returning to FIG. 2A, the body 20 also includes one or more sets of detent pockets, preferably having a first set of proximal detent pockets 40 adjacent the finger grip 50, and a second set of distal detent pockets 42 at a more distal location on the body 20. Preferably, as best seen in FIG. 5C, the proximal detent pockets 40 have sloping distal edges 40a and substantially blunt proximal edges 40b. Relatively shallow recesses 41 are provided at the bottom of the proximal detent pockets 40, thereby defining substantially blunt distal corners 41a between the sloping distal edges 40a and the recesses 41. In addition, the distal detent pockets 42 have substantially blunt, and preferably oblique, proximal edges 42b that preferably define generally acute proximal corners 42c.

Figure 3A:
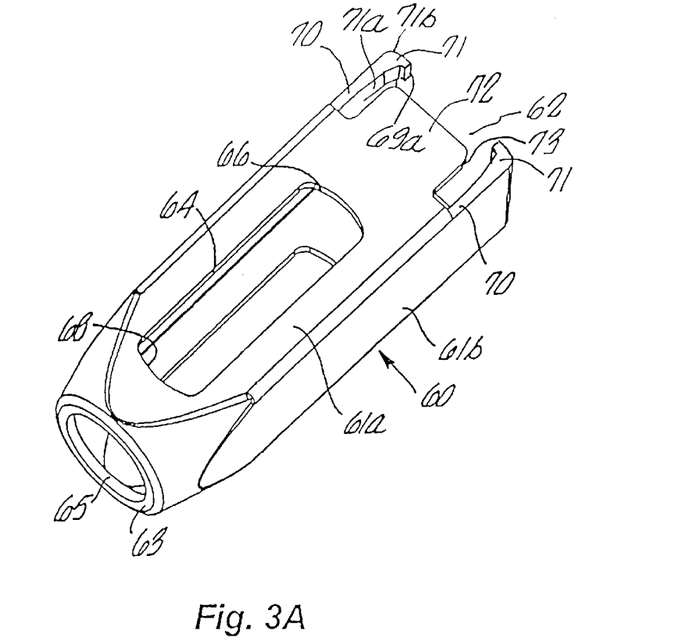
FIGS. 3A and 3B are perspective views of the shield of the syringe guard of FIG. 1.
Figure 3B:
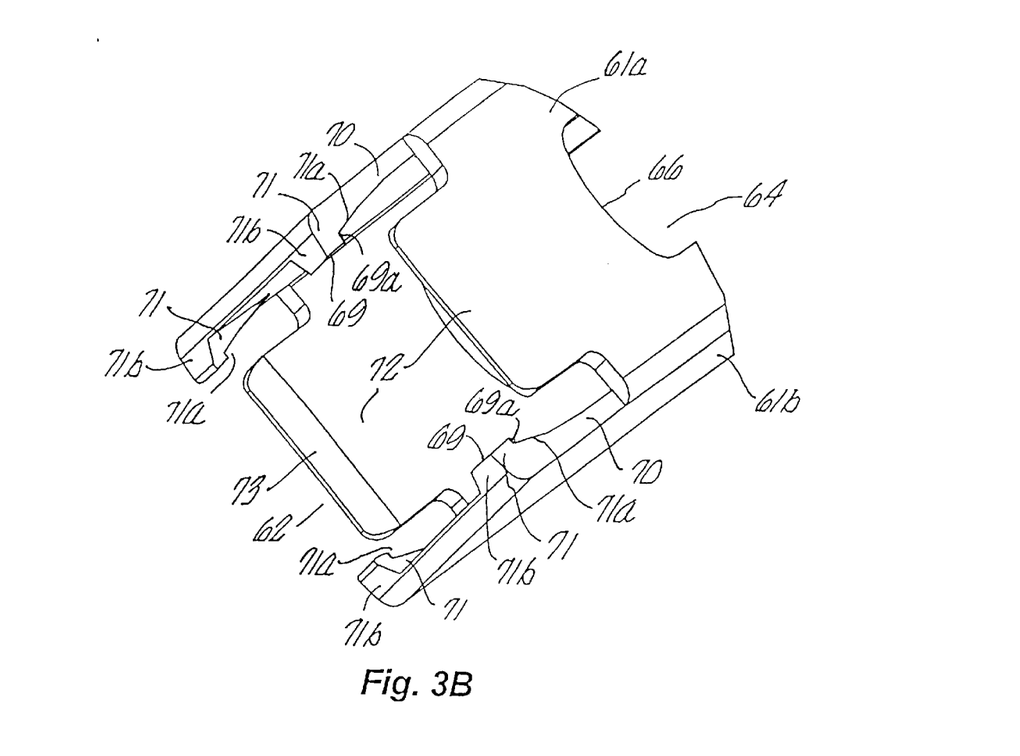

With particular reference to FIGS. 3A and 3B, the shield 60 is a tubular member adapted to slidably fit on the body 20, preferably having a substantially rectangular interior shape which conforms to the shape of the body 20. The shield 60 includes four side walls 61a, 61b, an open proximal end 62, and an open distal end 63. The shield 60 has a pair of detent arms 70 and a plurality of detents 71 attached to or preferably integrally molded to the side walls 61b. Assembly tabs 72 with sloping or ramped interior surfaces 73 are molded into and extend proximally from the side walls 61a.

The detents 71 preferably have shapes similar to features of the detent pockets 40, 42 in the body 20. Proximal edges 71b of the detents 71 are blunt, and preferably oblique, to define acute proximal corners 71c. The proximal edges 71b facilitate engagement with the proximal surfaces 42b of the distal detent pockets 42, the proximal corners 71c of the detents 71 preferably positively engaging the proximal corners 42c of the distal detent pockets 42, as described further below. The distal edges 71a are sloped and terminate in substantially blunt portions 69 defining substantially blunt distal corners 69a, corresponding to the recesses 41 and blunt corners 41a in the proximal detent pockets 40. In addition, the detent arms 70 may include indents 170 for controlling the flexural strength of the detent arms 70, as the arms 70 may vary in size and thickness in embodiments adapted to accommodate a variety of syringes.

At least one wall 61a of the shield 60, and preferably the two opposite walls 61a, include an elongate opening or window 64 therethrough. The window 64 allows observation of the pre-filled syringe 90 received in the body 20, and also provides a traveling slot for the stop tab 39 on the body 20. The window 64 has a proximal wall 66 and a distal wall 68 defined by the wall 61a which limit the relative movement of the shield 60 with respect to the body 20, as explained further below. Alternatively, the window 64 may be divided by a cross-member (not shown) molded into the wall 61a which extends transversely across the window 64 if desired to further limit the movement of the shield 60.

Optionally, the side walls 61a, 61b may include wings, a ring or similar finger holds (not shown) extending transversely outward from the shield 60 to ease movement of the shield 60 in relation to the body 20. In addition, the side walls 61a, 61b may provide a flat surface onto which a label may be applied, for example, to identify the drug or other fluid contained within the pre-filled syringe 90 received within the guard 10, or an embossed pattern may be molded, possibly including a name or a logo.

Figure 4:
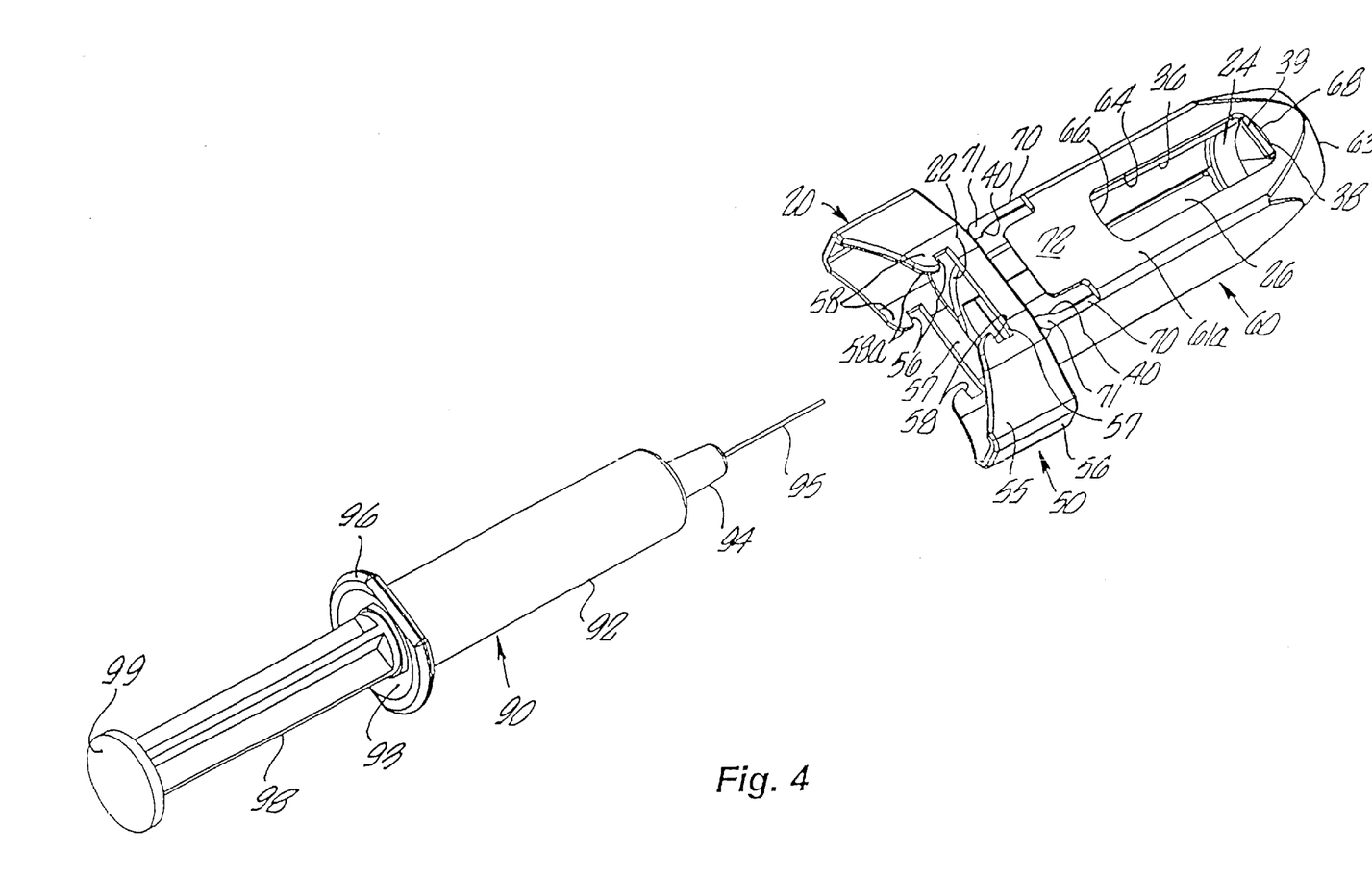
FIG. 4 is a perspective view of the pre-assembled syringe guard about to receive a unit dose pre-filled syringe therein.

Turning to FIG. 4, the guard 10 is normally provided with the body 20 and shield 60 pre-assembled. To assemble the guard 10, the distal end 24 of the body 20 (see FIG. 2A) is inserted into the open proximal end 62 (see FIG. 3A) of the shield 60, with the window 36 in the body 20 aligned with the side wall 61a of the shield 60 having the window 64 therein. As the body 20 is inserted, the sloped distal edge 39b of the stop tab 39 (and similarly the stop tab and window on the opposite side) slidably engages the tapered interior edge 73 of the assembly tab 72 on the shield 60 (see FIG. 3B).

Because the stop tab 39 is provided on the cantilever member 38, as the sloped distal edge 39b of the stop tab 39 engages the assembly tab 72, the cantilever member 38 is deflected inward, allowing the stop tab 39 to pass under the wall 61a. The radiused outer edge 39c of the stop tab 39 facilitates the stop tab 39 substantially smoothly gliding under the wall 61a without substantial abrasion or other damage to the stop tab 39 and/or to the shield 60. Once the stop tab 39 passes under the wall 61a, it enters the window 64. The cantilever member 38 resiliently returns to its original outward position, such that the stop tab 39 may engage the proximal and distal walls 66, 68 of the window 64.

Together, the stop tab 39 and window 64 allow the shield 60 to slidably move in relation to the body 20, but substantially define the limits of that relative movement. The shield 60 may slide proximally and distally until the stop tab 39 abuts the distal and proximal walls 68, 66, respectively, of the window 64. Specifically, when the stop tab 39 engages the distal wall 68 of the window 64 (see FIGS. 5A–5C), the shield 60 is in a proximal or unguarded position. When the stop tab 39 engages the proximal wall 66 of the window 64 (see FIGS. 6A–6C), the shield 60 is in a distal or guarded position. The proximal and distal walls 66, 68 of the window 64 and the proximal and distal edges 39b, 39a of the stop tab 39 may have substantially similar shapes across their widths, e.g., corresponding concave and convex shapes, respectively, to provide substantial engagement therebetween.

Figure 5A:
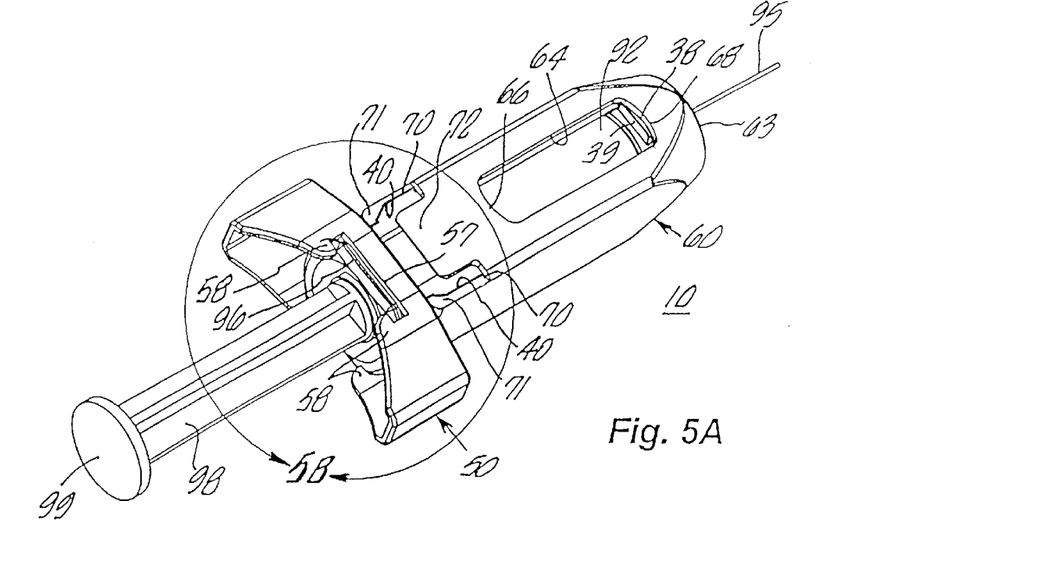
FIGS. 5A and 5B are perspective views of the syringe guard holding a pre-filled syringe, with the shield in an unguarded position, ready to be used to deliver medication to a patient.
Figure 5B:
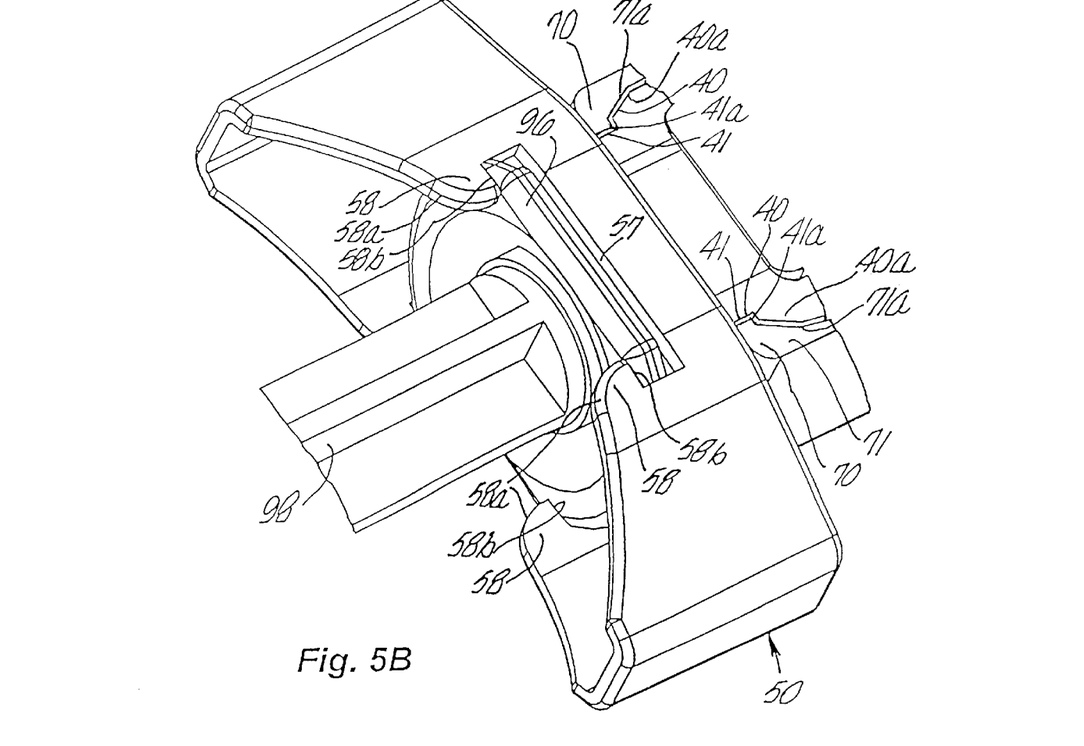
Figure 5C:
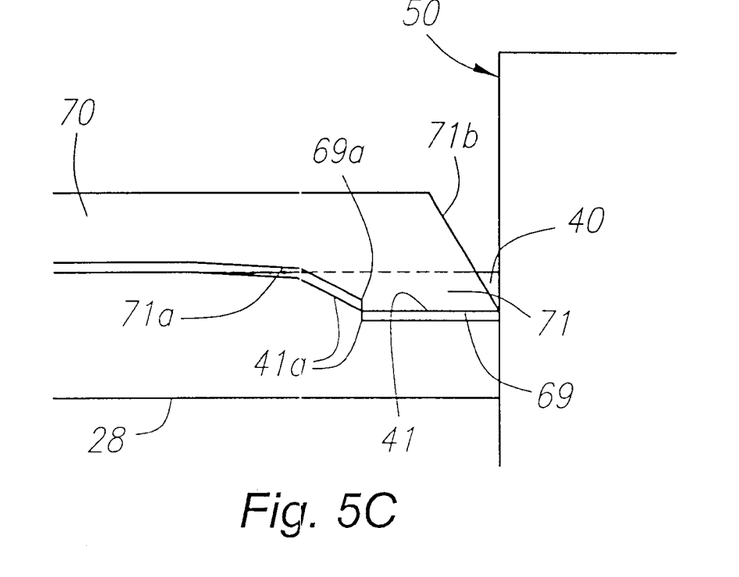
FIG. 5C is a detail of the syringe guard of FIG. 5A, showing the cooperation of the detents and the proximal detent pockets in the unguarded position.

Turning to FIGS. 5A–5C, when the stop tab 39 approaches the distal wall 68 of the window 64, the cooperating detents 71 and proximal detent pockets 40 engage to retain the shield 60 in the unguarded position. The sloping distal edges 71a of the detents 71 may engage the sloping distal edges 40a of the proximal detent pockets 40 on the body 20, and the distal corners 69a of the detents 71 substantially engage the distal corners 41a of the detent pockets 40, thereby preventing the shield 60 from moving distally.

Figure 1:
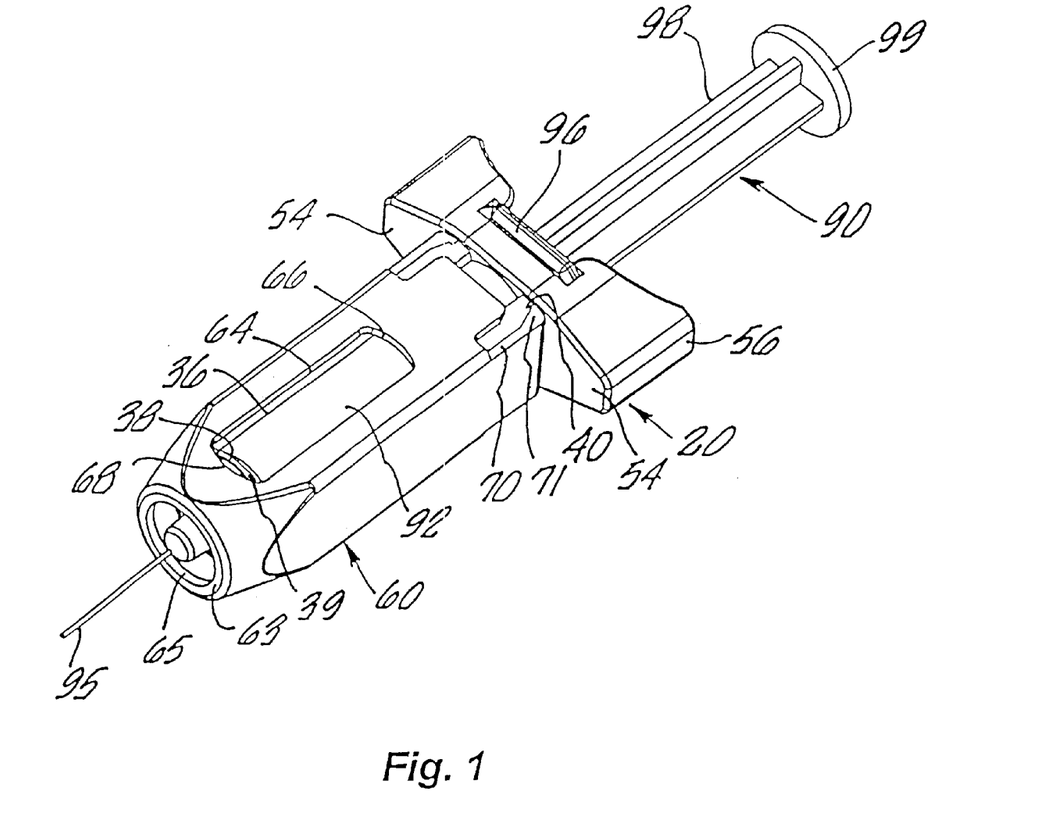
FIG. 1 is a perspective view of a first preferred embodiment of a syringe guard in accordance with the present invention, holding a unit dose pre-filled syringe.
Figure 7:
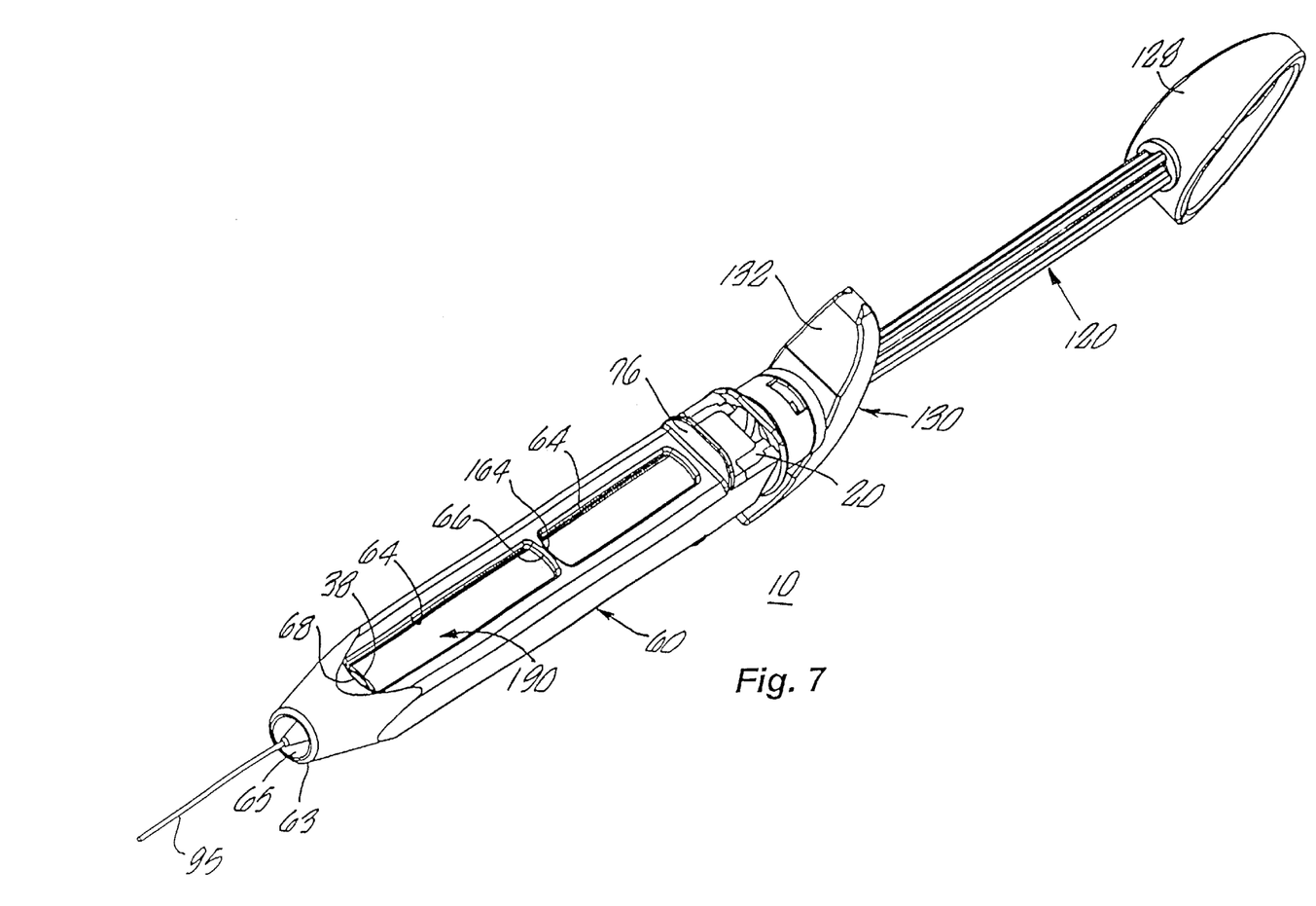
FIG. 7 is a perspective view of a second preferred embodiment of the syringe guard holding a unit dose ampule, with the shield in an unguarded position, ready to be used to deliver medication to a patient.

Returning to FIG. 4, once assembled, the guard 10 is ready to receive a medical cartridge, such as a conventional unit dose pre-filled syringe 90. Although the pre-filled syringe 90 shown in FIGS. 1 and 4 is the preferred delivery system for use with a syringe guard in accordance with the present invention, it will be appreciated that a syringe guard including the features described herein may be used for other pre-filled or unit dose delivery systems, and that the term "cartridge" includes other such known systems. For example, as shown in FIG. 7, a syringe guard 10 is shown for receiving an ampule 190 that does not include its own plunger. Similarly, a syringe guard in accordance with the present invention may be provided for receiving an ampule without its own needle (not shown), as may be used for aspirating dental syringe systems. Additional information on other cartridges and their guards that may include features of a syringe guard in accordance with the present invention may be found in U.S. Pat. No. 5,624,400 issued to Firth et al., and in co-pending U.S. patent applications Ser. Nos. 08/942,938, filed Oct. 2, 1997, and Ser. No. 08/814,199, filed Mar. 10, 1997. The disclosures of these references are expressly incorporated herein by reference.

The pre-filled syringe 90 generally has a substantially smooth-walled cylindrical barrel 92, a distal end or hub 94 including a hypodermic needle 95, a needle cover or cap (not shown), an enlarged proximal end 93 having a flange 96, and a plunger 98. The flange 96 generally includes a flat edge 96a in a predetermined orientation with a label or graduation marks 92a on the barrel 92 of the pre-filled syringe 90. Preferably, the flange 96 includes two opposite flat edges 96a extending between two curved edges 96b, thereby defining a generally rectangular-shaped finger grip 96. The flange 96 may have a sufficiently large width to provide a finger grip for the pre-filled syringe 90, or may simply be a small lip to facilitate manufacturing, for example, on a filling line.

The distal end 94 of the pre-filled syringe 90 is inserted into the recess 51 of the finger grip 50 and the open proximal end 22 of the body 20. The pre-filled syringe 90 enters the cavity 26 and progresses distally until the distal end 94 of the pre-filled syringe 90 becomes substantially coextensive with and/or directly engages the distal end 24 of the body 20. The distal end 94 of the pre-filled syringe 90 may simply abut the distal end 24 of the body 20, or alternatively the distal end 94 may partially enter the opening 34 and engage the collar 32, thereby providing additional protection from lateral movement of the pre-filled syringe 90 (see FIGS. 1 and 6A).

As the pre-filled syringe 90 becomes fully encapsulated within the cavity 26, the flange 96 on the proximal end 93 of the pre-filled syringe 90 contacts the locking detents 58 on the finger grip 50. The locking detents 58 have tapered proximal edges 58a, allowing the pre-filled syringe 90 to be directed further distally, the flange 96 moving the locking detents 58 aside and entering the slot 57. As is shown in FIGS. 5A and 5B, the locking detents have blunt distal edges 58b which prevent the pre-filled syringe 90 from being removed proximally from the slot 57, thereby substantially permanently locking the pre-filled syringe 90 into the body 20. Thus, the slots 57 preferably substantially permanently lock the proximal end 93 of the pre-filled syringe 90 within the finger grip 50, thereby preventing axial (i.e. proximal and/or distal) movement of the pre-filled syringe 90 within the guard 10.

Although the pre-filled syringe 90 is considered substantially permanently encapsulated within the guard 10, the material of the finger grip 50 may have sufficient flexibility to allow a tool (not shown) to move the detents 58 to allow the pre-filled syringe 90 to be removed from the body 20. Preferably, the tool applies a distal force to each of the proximal edges 56a of the outer surface 56, causing the lateral surfaces 55 and detents 58 to expand outward to release the flange 96. Alternatively, the tool may engage the lateral surfaces 55 directly and force them outward to release the flange 96 from the slots 57.

Thus, if an incorrect pre-filled syringe 90 is inserted into the guard 10 during factory assembly, it may be released from the guard 10 without damaging the guard 10 and/or the pre-filled syringe 90, thereby allowing both to be reused. This may be particularly important for pre-filled glass syringes for which the flange 96 is often structurally the weakest point of the pre-filled syringe 90. Thus, a pre-filled glass syringe 90 may be releasably encapsulated within the guard 10, allowing removal of the pre-filled syringe 90 under certain controlled conditions. The finger grip 50, however, is sufficiently rigid that, during normal use for example by a medical professional, the pre-filled syringe 90 is preferably not removable from the guard 10.

In addition, the generally rectangular-shaped flange 96 may establish a preferred orientation for the pre-filled syringe 90 to be received in the guard 10. Preferably, the shape of the flange 96 allows the pre-filled syringe 90 to be received within the slots 57 only in an orientation that allows the label 92a to be visible through the window 64 of the guard 10 during use (see FIG. 5A). For example, the detents 58 may engage the opposing flat edges 96a of the flange 96 (not shown), thereby preventing the pre-filled syringe 90 from being rotated about its longitudinal axis within the body 26. Alternatively, the finger grip 50 may be provided with any symmetrical or predetermined shape adapted to correspond substantially to the shape of a flange on a cartridge being received therein, thereby encapsulating the cartridge within the body 20 in a predetermined orientation about the longitudinal axis of the cartridge. For example, an elliptical or oval finger grip (not shown) may provide an appropriate alternative shape, or a round finger grip (not shown) may be provided if it has a recess having a shape corresponding to that of the flange on the cartridge.

Turning particularly to FIGS. 1 and 5A, once the pre-filled syringe 90 is locked into the guard 10, the needle 95 and the needle cover (not shown) extend through the opening 34 on the collar 32 and the opening 65 on the distal end 63 of the shield 60. The distal end 63 of the shield 60 has a generally tapered configuration defining an opening 65 through which the needle 95 may extend. Preferably, the length of the shield 60 is substantially coextensive with the barrel 92 of the pre-filled syringe 90, allowing the full length of the needle 95 to extend beyond the distal end 62 of the shield 60, but protecting the hub 94 of the pre-filled syringe 90.

The opening 65 is generally circular and has a diameter larger than that of the syringe barrel 92 and/or hub 94, and may be provided with a variety of diameters or configurations to facilitate use of the pre-filled syringe 90. For example, the diameter of the opening 65 may be sufficiently large to allow a luer adapter (not shown) or other alternative distal tip to be provided on the pre-filled syringe 90 or to be attached to the hub 94 during use. Most preferably, however, the opening 65 has a diameter sufficiently small to minimize the risk of accidental sticks, for example, to prevent a finger from being directed into the shield 60 after use.

The pre-filled syringe 90 encapsulated within the guard 10 may then be used to deliver the medication in the barrel 92. The medical professional typically holds the pre-filled syringe 90 by placing his or her index finger on a finger ledge 54, his or her middle finger on the other finger ledge 54, and his or her thumb on the end 99 of the plunger 98. The cover (not shown) is removed, the needle 95 is injected or otherwise introduced into the patient, and the medication is delivered by directing the plunger 98 distally with the thumb. As can be seen from FIGS. 1 and 5A, the windows 64 and 36 facilitate observation of the barrel 92 of the pre-filled syringe 90, allowing the user to closely monitor delivery of the medication. The finger grip 50 also preferably has a sufficiently large size relative to the flange 96 to provide improved manipulation by the user as compared to using the pre-filled syringe 90 alone.

After the medication is dispensed, the needle 95 is withdrawn from the patient, and the shielding feature of the guard 10 may be engaged. The user holds the body 20, typically by placing his ring finger on the gripping surface 56 adjacent his middle finger, and moving his thumb from the plunger 98 to the other gripping surface 56. The index and middle fingers, already adjacent the side walls 61b of the shield 60, grip the walls 61b and are moved distally, thereby sliding the shield 60 distally until it reaches the guarded position, shown in FIG. 6A. Alternatively, while one hand holds the finger grip 50, the shield 60 may be directed to the guarded position with the free hand of the user.

Figure 6A:
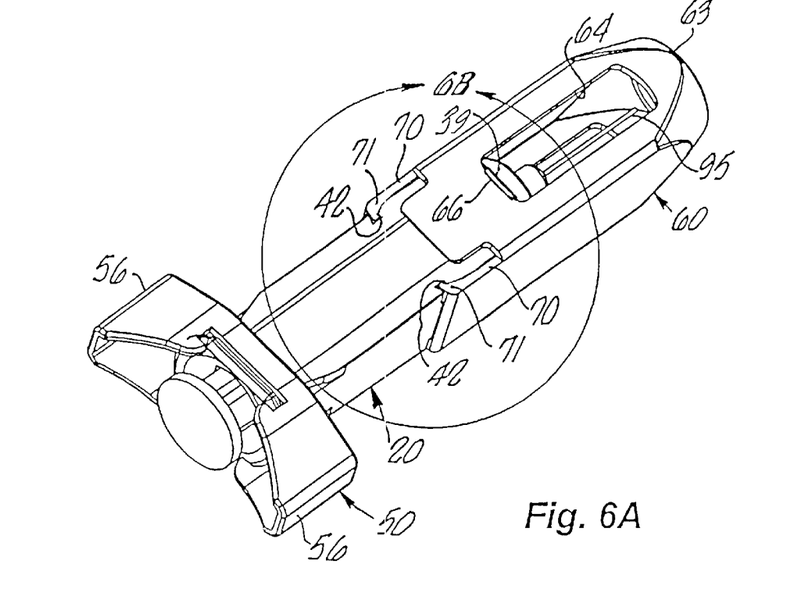
FIGS. 6A and 6B are perspective views of the syringe guard holding a pre-filled syringe, with the shield locked in a guarded position after medication has been dispensed from the pre-filled syringe.
Figure 6B:
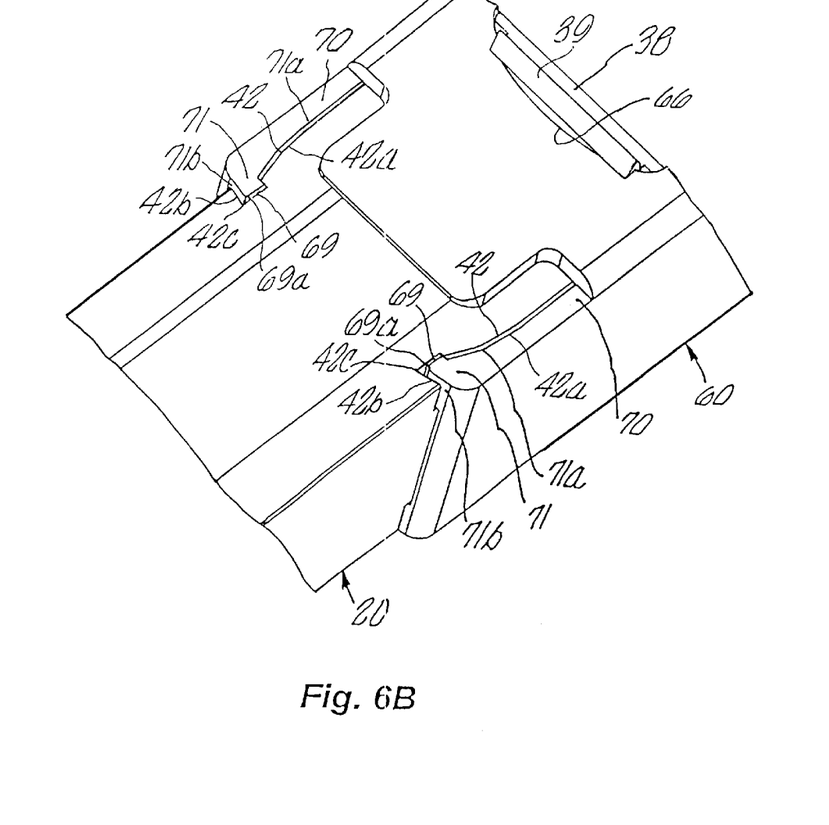
Figure 6C:
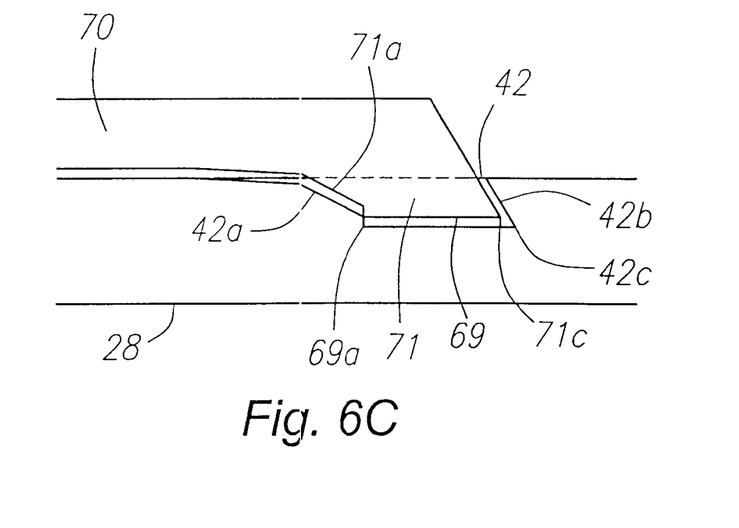
FIG. 6C is a detail of the syringe guard of FIG. 6A, showing the cooperation of the detents and the distal detent pockets in the guarded position.

Because the cooperating detents 71 and detent pockets 40 hold the shield 60 in the unguarded position, force must be applied to move the shield 60 distally. The blunt recesses 41 in the detent pockets 40 and the blunt portion 69 on the detents 71 create an initial resistance to distal movement of the shield 60 with respect to the body 20, thereby substantially preventing unintentional activation of the shield 60. Once this initial resistance is overcome, the sloping distal edges 71a of the detents 71 may slidably engage the sloping distal edges 40a of the detent pockets 40. The detent arms 70 move transversely outward as the detents 71 move distally up the sloping edges 40a until the detents 71 leave the detent pockets 40. The shield 60 may then be moved freely, the stop tab 39 traveling along the window 64, until the stop tab 39 abuts the proximal wall 66 of the window 64, reaching the guarded position.

As shown in FIG. 6A, because of the predetermined location of the distal detent pockets 42 and the stop tab 39, when the stop tab 39 reaches the proximal wall 66 of the window 64, the detents 71 substantially simultaneously enter the distal detent pockets 42. The oblique proximal edges 71b of the detents engage the similarly shaped proximal edges 42b of the distal detent pockets 42, thereby preventing the shield 60 from being moved proximally. The corresponding shape of the engaged proximal edges 71b, 42b may also maximize bearing surface to prevent misalignment of the shield 60. If it is attempted to move the shield 60 proximally, i.e., towards the unguarded position, the proximal corners 71c of the detents 71 positively engage the proximal corners 42c in the distal detent pockets 42, thereby preventing substantial proximal movement of the shield 60.

Furthermore, because the stop tab 39 abuts the proximal wall 66 of the window 64, the shield 60 may not be moved distally beyond the guarded position. In particular, the blunt proximal edge 39b of the stop tab 39 substantially engages the proximal wall 66 of the window 64. If it is attempted to move the shield distally beyond the guarded position, the blunt shape of the proximal edge 39b of the stop tab 39 causes the cantilever member 38 to deflect slightly outward, thereby positively engaging the proximal wall 66 and ensuring that the shield 60 may not be directed further distally. Thus, by the simultaneous action of the stop tabs 39 and the cooperating detents 71 and detent pockets 42, the shield 60 is substantially permanently locked in the guarded position.

As can be seen from FIG. 6A, when the shield 60 is moved distally into the guarded position, the distal end 63 of the shield 60 passes over and substantially covers the needle 95. Once the shield 60 is locked in the guarded position, the needle 95 is no longer accessible, thereby substantially eliminating the risk of accidental sticks and preventing reuse of the pre-filled syringe 90. The guard 10 and pre-filled syringe 90 may then be disposed of safely.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A guard for a medical cartridge, comprising:
    a body having a cavity extending axially between an open proximal end and a distal end of said body, said cavity being adapted to receive a medical cartridge therein;
    a shield slidably attached to said body, said shield having proximal and distal ends, said distal end having an opening through which a needle may extend when said shield is in an unguarded position, said shield being adapted to slide distally in relation to said body between said unguarded position and a guarded position wherein the needle is covered by said shield;
    a first set and a second set of detent pockets formed in said body, said second set being located distally from said first set, said first set of detent pockets comprising generally sloped distal edges, said distal edges terminating in substantially blunt distal corners; and
    a plurality of detents on said shield adapted to engage said detent pockets, said plurality of detents includes generally sloped distal edges, said distal edges terminating in substantially blunt distal corners;
    whereby when said shield is in said unguarded position, said distal corners of said detents substantially engage said distal corners of said detent pockets to create an initial resistance to movement of said shield towards said guarded position.

2. The guard of claim 1, wherein said distal detent pockets have substantially blunt proximal edges defining proximal corners, and said detents have oblique proximal edges defining substantially acute proximal corners;
    whereby when said shield is moved to said guarded position, said proximal corners on said detents substantially engage said proximal corners in said detent pockets to prevent substantial proximal movement of said shield from said guarded position.

3. The guard of claim 1, further comprising:
    a stop tab extending substantially transversely from said body; and
    an elongate opening in said shield, said elongate opening being adapted to receive said stop tab therein, said stop tab being slidable in said elongate opening, thereby allowing said shield to slide between said unguarded and guarded positions.

4. The guard of claim 3, further comprising a semi-rigid cantilever member on said distal end of said body, said cantilever member having said stop tab integrally molded thereon.

5. The guard of claim 3, wherein said cantilever member extends substantially proximally from said distal end of said body.

6. The guard of claim 3, wherein said stop tab has a generally sloped distal edge for facilitating initial assembly of said shield proximally over said body.

7. The guard of claim 3, wherein said stop tab has a substantially blunt or concave proximal edge for positively engaging a proximal wall of said elongate opening when said shield is in said guarded position.

8. The guard of claim 3, wherein said elongate opening comprises a window for facilitating observation of the cartridge received in said body.

9. The guard of claim 1, further comprising a finger grip on said proximal end of said body, said finger grip including a locking mechanism for substantially securing the cartridge within said cavity.

10. The guard of claim 9, wherein said finger grip is integrally molded to said proximal end of said body.

11. The guard of claim 1, wherein said distal end of said body comprises an opening through which a needle on the cartridge may extend when the cartridge is received in said cavity.

12. A guard for a medical cartridge, comprising:
    a body having a cavity extending axially between an open proximal end and a distal end of said body, said cavity being adapted to receive a medical cartridge therein;

a shield slidably attached to said body, said shield having proximal and distal ends, said distal end having an opening through which a needle may extend when said shield is in an unguarded position, said shield being adapted to slide distally in relation to said body between said unguarded position and a guarded position wherein the needle is covered by said shield;

cooperating detents and detent pockets formed in said body and said shield for mutually engaging to hold said shield in said guarded position, said detent pockets having substantially oblique proximal edges defining proximal corners, said detents having substantially oblique proximal edges defining substantially acute proximal corners;

whereby when said shield is moved to said guarded position, said proximal corners on said detents substantially engage said proximal corners in said detent pockets to prevent substantial proximal movement of said shield from said guarded position.

13. The guard of claim 12, wherein said cooperating detents and detent pockets comprise:

first and second sets of detent pockets formed in said body, said second set being located distally from said first set; and a plurality of detents on said shield adapted to engage said detent pockets, said unguarded position being defined by said detents engaging said first set of detent pockets, and said guarded position being defined by said detents engaging said second set of detent pockets.

14. The guard of claim 13, wherein:

said detents include generally sloped distal edges, said distal edges terminating in substantially blunt distal corners; and said first set of detent pockets comprise generally sloped distal edges, said distal edges terminating in substantially blunt distal corners;

whereby when said shield is in said unguarded position, said distal corners of said detents substantially engage said distal corners of said detent pockets to create an initial resistance to movement of said shield towards said guarded position.

15. The guard of claim 13, wherein said plurality of detents are integrally molded to said shield adjacent said proximal end.

16. The guard of claim 12, further comprising a finger grip on said proximal end of said body, said finger grip including a locking mechanism for substantially securing the cartridge within said cavity.

17. The guard of claim 16, wherein said finger grip is integrally molded to said proximal end of said body.

18. The guard of claim 12, wherein said distal end of said body comprises an opening through which a needle on the cartridge may extend when the cartridge is received in said cavity.

19. The guard of claim 12, further comprising:

a stop tab extending substantially transversely from said body; and an elongate opening in said shield, said elongate opening being adapted to receive said stop tab therein, said stop tab being slidable in said elongate opening, thereby allowing said shield to slide between said unguarded and guarded positions.

20. The guard of claim 19, further comprising a semi-rigid cantilever member on said distal end of said body, said cantilever member having said stop cab integrally molded thereon.

21. A guard for a medical cartridge, comprising:

a body having a cavity extending axially between an open proximal end and a distal end of said body, said cavity being adapted to receive a medical cartridge therein;

a shield slidably attached to said body, said shield having proximal and distal ends, said distal end having an opening through which a needle may extend when said shield is in an unguarded position, said shield being adapted to slide distally in relation to said body between said unguarded position and a guarded position wherein the needle is covered by said shield;

cooperating detents and detent pockets formed in said body and said shield for mutually engaging to hold said shield in said guarded position;

a semi-rigid cantilever member on said distal end of said body, said cantilever member having a stop tab extending substantially transversely therefrom; and an elongate opening in said shield, said elongate opening being adapted to receive said tab therein, said stop tab being slidable in said elongate opening, thereby allowing said shield to slide between said unguarded and guarded positions.

22. The guard of claim 21, wherein said cantilever member extends substantially proximally from said distal end of said body.

23. The guard of claim 21, wherein said stop tab has a generally sloped distal edge for facilitating initial assembly of said shield proximally over said body.

24. The guard of claim 21, wherein said stop tab has a substantially blunt or generally concave proximal edge extending substantially transversely outward and proximally from said body, for engaging a proximal wall of said elongate opening.

25. The guard of claim 21, wherein said elongate opening comprises a window for facilitating observation of the cartridge received in said body.

26. The guard of claim 21, wherein said body includes a window adjacent said cantilever member for facilitating observation of the cartridge received in said body.

27. The guard of claim 21, further comprising a finger grip on said proximal end of said body, said finger grip including a locking mechanism for substantially securing the cartridge received in said cavity.

28. The guard of claim 27, wherein said finger grip is integrally molded to said proximal end of said body.

29. The guard of claim 21, wherein said distal end of said body comprises an opening through which a needle on the cartridge may extend when the cartridge is received in said cavity.

30. The guard of claim 21, wherein said body has a substantially rectangular cross-section.

31. The guard of claim 21, further comprising a finger grip plug lockably attachable to said proximal end of said body, thereby enclosing said cavity and encapsulating the cartridge received therein.

32. The guard of claim 31, further comprising a plunger having a distal end attachable to a piston in the cartridge, thereby allowing said plunger to slidably direct the piston distally and proximally.

33. The guard of claim 31, wherein said finger grip plug includes a plurality of locking detents, and said proximal end of said body includes tapered pockets adapted to receive said locking detents for locking said finger grip plug to said body.

34. The guard of claim 33, wherein said locking detents on said finger grip have distal edges adapted to engage a proximal end of the cartridge received within said cavity, thereby preventing substantial proximal movement of the cartridge within said cavity.

35. A method for assembling a safety syringe system including a body having a cavity extending between an open proximal end and a distal end of the body, and a shield having open proximal and distal ends, the method comprising the steps of:

aligning an assembly tab on the proximal end of the shield with a stop tab on a cantilever member on the distal end of the body;

inserting the distal end of the body into the proximal end of the shield, the stop tab slidably engaging the assembly tab, thereby deflecting the cantilever member inward as the stop tab passes under a wall of the shield; and advancing the body distally until the stop tab enters an elongate window in the wall of the shield, the cantilever member resiliently returning to its original position.

36. The method of claim 35, wherein the stop tab has a generally sloped distal edge extending to a radiused outer edge such that when the body is advanced into the shield, the radiused outer edge substantially smoothly glides under the wall of the shield.

37. The method of claim 35, comprising the additional step of directing the shield proximally to an unguarded position such that detents on the shield enter proximal detent pockets in the body.

38. The method of claim 37, wherein the detents include generally sloping distal edges terminating in substantially blunt distal corners, and the proximal detent pockets include generally sloping distal edges terminating in substantially blunt distal corners, whereby when the shield is in the unguarded position, the distal corners of the detents substantially engage the distal corners of the detent pockets to create an initial resistance to distal movement of the shield.

39. The method of claim 35, wherein the safety syringe system includes a medical cartridge, and the method comprises the additional steps of:

inserting a distal end of the cartridge into the proximal end of the body;

advancing the cartridge distally into the body until a locking mechanism on the body engages the cartridge to substantially permanently encapsulate the cartridge in the body.

40. The method of claim 39, wherein the cartridge includes a flange on its proximal end, and the locking mechanism comprises locking detents on the proximal end of the body for engaging the flange.

* * * * *

UNITED STATES PATENT AND TRADEMARK OFFICE
CERTIFICATE OF CORRECTION

PATENT NO. : 6,030,366  
DATED : February 29, 2000  
INVENTOR(S) : David W. Mitchell Page 1 of 1

It is certified that error appears in the above-identified patent and that said Letters Patent is hereby corrected as shown below:

Column 1,  
Line 8, please change "un t" to -- unit --.  
Line 56, please change "Others," to -- Others --.

Column 5,  
Line 54, please change "56E" to -- 56. --.

Column 10,  
Line 27, please change "distal end 62" to -- distal end 63 --.

Signed and Sealed this

Twenty-fifth Day of December, 2001

*Attest:*

JAMES E. ROGAN  
*Attesting Officer*     *Director of the United States Patent and Trademark Office*